(12) United States Patent
Stoicescu

(10) Patent No.: US 8,247,422 B2
(45) Date of Patent: Aug. 21, 2012

(54) USE OF CONDENSED PYRIMIDINE DERIVATIVES FOR THE TREATMENT OF RHEUMATOID ARTHRITIS

(76) Inventor: Dan Stoicescu, Dully (CH)

(*) Notice: Subject to any disclaimer, the term of this patent is extended or adjusted under 35 U.S.C. 154(b) by 189 days.

(21) Appl. No.: 12/449,448

(22) PCT Filed: Feb. 13, 2008

(86) PCT No.: PCT/EP2008/051731
§ 371 (c)(1),
(2), (4) Date: Dec. 22, 2009

(87) PCT Pub. No.: WO2008/098957
PCT Pub. Date: Aug. 21, 2008

(65) Prior Publication Data
US 2010/0160329 A1    Jun. 24, 2010

(30) Foreign Application Priority Data
Feb. 14, 2007 (EP) .................................. 07102410

(51) Int. Cl.
*A61K 31/517* (2006.01)
(52) U.S. Cl. .............. 514/258.1; 514/257; 514/256; 514/247; 514/183; 544/253; 544/245; 544/242
(58) Field of Classification Search .................. None
See application file for complete search history.

(56) References Cited

U.S. PATENT DOCUMENTS

| | | | |
|---|---|---|---|
| 2,512,572 A | 6/1950 | Smith. Jr. et al. | |
| 4,077,957 A | 3/1978 | Piper et al. | |
| 4,684,653 A | 8/1987 | Taylor et al. | |
| 5,344,932 A | 9/1994 | Taylor | |
| 5,698,556 A | 12/1997 | Chan | |
| 7,718,660 B2 * | 5/2010 | Stoicescu | 514/258.1 |
| 2006/0083681 A1 | 4/2006 | Purohit et al. | |
| 2007/0287704 A1 | 12/2007 | Dollinger et al. | |
| 2008/0153833 A1 | 6/2008 | Dollinger et al. | |

FOREIGN PATENT DOCUMENTS

| | | |
|---|---|---|
| GB | 2070607 A | 9/1981 |
| JP | 63-218666 A | 9/1988 |
| WO | WO 91/19700 A1 | 12/1991 |
| WO | WO 2007/020277 A2 | 2/2007 |

OTHER PUBLICATIONS

"Autoimmune disorders" (retrieved from nlm.nih.gov on Nov. 9, 2011).*
"Overview of Allergy and Hypersensitivity" in the Merck Manual (retrieved from merckmanual.com on Nov. 9, 2011).*
"Animal models of rheumatoid arthritis and their relevance to human disease" by Kannan et al., Pathophysiology 12, 167-181 (2005).*
"A Delicate Balance: What Changes in the Immune System Trigger Type 1 Diabetes?" by the Joslin Diabetes Center, Harvard Medical School (retrieved from joslin.org on Nov. 9, 2011).*
"Arthritis" by Symptomfind.com (retrieved Nov. 9, 2011).*
"Crohn's Disease Causes & Risk Factors" by Symptomfind.com (retrieved Nov. 9, 2011).*
"Autoimmune Diseases" by Ross (retrieved from lvhn.org on Nov. 9, 2011).*
Office Action from U.S. Appl. No. 11/663,567 dated Feb. 18, 2009.
Office Action from U.S. Appl. No. 12/080,844 dated Jan. 8, 2010.
Boger et al. "Phenyl Selenoesters as Effective Precursors of Acyl Radicals for Use in Intermolecular Alkene Addition Reactions" *J. of Organic Chem.*, vol. 54:8 (Apr. 14, 1989).
Mooney et al. "Photochemistry and Photophysics of Surfactant *trans*-Stilbenes in Supported Multilayers and Films at the Air-Water Interface" *J. Am. Chem. Soc.* vol. 106: 5659-5667 (1984).
Quinlivan et al. "Methylenetetrahydrofolate Reductase 677C→T Polymorphism and Folate Status Affect One-Carbon Incorporation into Human DNA Deoxynucleosides$^{1,2}$" *J. Nutr.* vol. 135:389-396 (Mar. 2005).
Smith, "Organic Synthesis: Retrosynthesis, Sterochemistry and Conformations" McGraw-Hill, Inc. (1994).
International Search Report from PCT/EP2006/065380, mailed Feb. 22, 2007.
Office Action from U.S. Appl. No. 11/663,567 dated Aug. 13, 2008.
Office Action from U.S. Appl. No. 11/663,567 dated Aug. 28, 2009.
Office Action from U.S. Appl. No. 12/080,842 dated Aug. 31, 2009.

\* cited by examiner

*Primary Examiner* — Anish Gupta
*Assistant Examiner* — Theodore R West
(74) *Attorney, Agent, or Firm* — Wolf, Greenfield & Sacks, P.C.

(57) ABSTRACT

The invention relates to the use of a compound of the formula (I), or a pharmaceutically acceptable salt thereof, for the manufacture of a medicament for use in modulating an immune or inflammatory response: wherein: Z=O or S; n=1-3; $R^3$=—$CO_2R^8$, —C(O)$SR^8$, —C(O)$NHR^8$, —C(S)$OR^8$, —C(S)$SR^8$, —C(S)$NHR^8$, —C(NH)$SR^8$ or —C(NH)$NHR^8$, wherein $R^8$ is —H or alkyl; $R^4$=—H, —$CH_2R^5$ or —$CH_2CH_2R^5$, wherein $R^5$ independently has one of the meanings of $R^3$; B=—$NR^2$—, —$CH_2NR^2$—, —$CH_2CH_2NR^2$—, —$CH_2CHR^7$— or —$CH_2O$—, wherein $R^2$ is H or a $C_{1-3}$ alkyl, alkenyl or alkynyl group, and $R^7$ is H or a $C_{1-3}$ alkyl or alkoxy group; A=wherein $R^1$=—$NH_2$ or —OH, C and D are each, independently, a 5- or 6-membered, substituted or unsubstituted, aromatic or non-aromatic ring which may also contain one or more heteroatoms, and C is connected to group B in any available position.

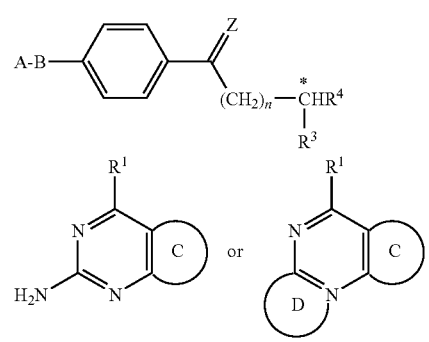

15 Claims, 3 Drawing Sheets

* P < 0.05 higher for vehicle treated mice than for test compound-treated or for methotrexate-treated mice.

Mean red blood cell counts at the end of the study

* Use of methotrexate led to significantly lower red blood cell counts ($p < 0.05$) by ANOVA with Tukey post-hoc test

USE OF CONDENSED PYRIMIDINE DERIVATIVES FOR THE TREATMENT OF RHEUMATOID ARTHRITIS

RELATED APPLICATIONS

This application is a national stage filing under 35 U.S.C. §371 of International Application No. PCT/EP2008/051731, filed Feb. 13, 2008, which claims priority European Application No. 07102410.3, filed Feb. 14, 2007. The contents of each of these applications are incorporated herein by reference in their entireties for all purposes.

The present invention relates to immunosuppressive therapy and to new treatments for autoimmune and inflammatory diseases. In a preferred embodiment, the present invention relates to new drugs for the treatment of rheumatoid arthritis.

Rheumatoid arthritis (RA) is a chronic, inflammatory autoimmune disease. It is characterised by progressively more debilitating pain and destruction of the joints, starting especially with the hands, feet and wrists. However, being a systemic disease, inflammation can also occur in extra-articular tissues such as the skin, heart, lungs and eyes. The World Health Organisation reports that prevalence of RA varies between 0.3 and 1%, being more common in women. Sufferers are more frequently over the age of 40 (although they can be diagnosed at any age), and at least 50% of patients in developed countries are unable to maintain full-time employment within 10 years of onset of the disease.

The precise cause of RA is not known. Genetic and a variety of environmental factors have been implicated, and it is believed that a complex combination of molecular pathways may be involved. In contrast, the mechanisms by which inflammation causes joint damage in RA are better understood. The focus of attack is the synovium, the soft tissue lining of the joint that isolates synovial fluid from the adjacent tissue. The healthy synovium contains fibroblasts that secrete the main constituents of synovial fluid into the joint cavity, as well as macrophages responsible for eliminating unwanted substances from this fluid. It also has a small number of blood vessels for providing nutrients to the nearby avascular cartilage, but no white blood cells.

Once activated, the autoimmune response leads to inflammation of the synovium, becoming filled with white blood cells that have entered via new blood vessels. Consumption of nutrients by the synovial cells is increased and production of synovial fluid is heightened. The whole joint capsule becomes swollen, and access of the cartilage to nutrients is blocked, leading to starvation and death of the cartilage cells. In addition, fibroblasts and macrophages are activated to secrete cytokines such as tumour necrosis factor α, or differentiate into destructive cells such as osteoclasts. The cartilage surface is digested and the underlying bone begins to wear away.

There is as yet no cure for RA, and existing treatments focus on the symptoms of the disease, which can vary widely between patients. General aims are to reduce pain and stiffness in the affected joints and to minimise joint damage, the latter being irreversible.

Non-steroidal anti-inflammatory drugs (NSAIDs) such as ibuprofen and meloxicam are used to reduce swelling and relieve minor pain and stiffness, but these do not slow the course of the disease and can cause stomach bleeding if taken over a long period of time. Corticosteroids may be injected into a joint to reduce pain and swelling in the case of a severe localised flare-up, but again these do not slow the progress of RA.

For the long term, patients are usually given a disease modifying anti-rheumatic drug (DMARD) to retard development of the disease and prevent joint damage. They can take weeks to months to start working, so the above medications giving short term relief are often also taken in these early stages. The DMARD class of drugs is chemically and pharmacologically very diverse; examples are shown below.

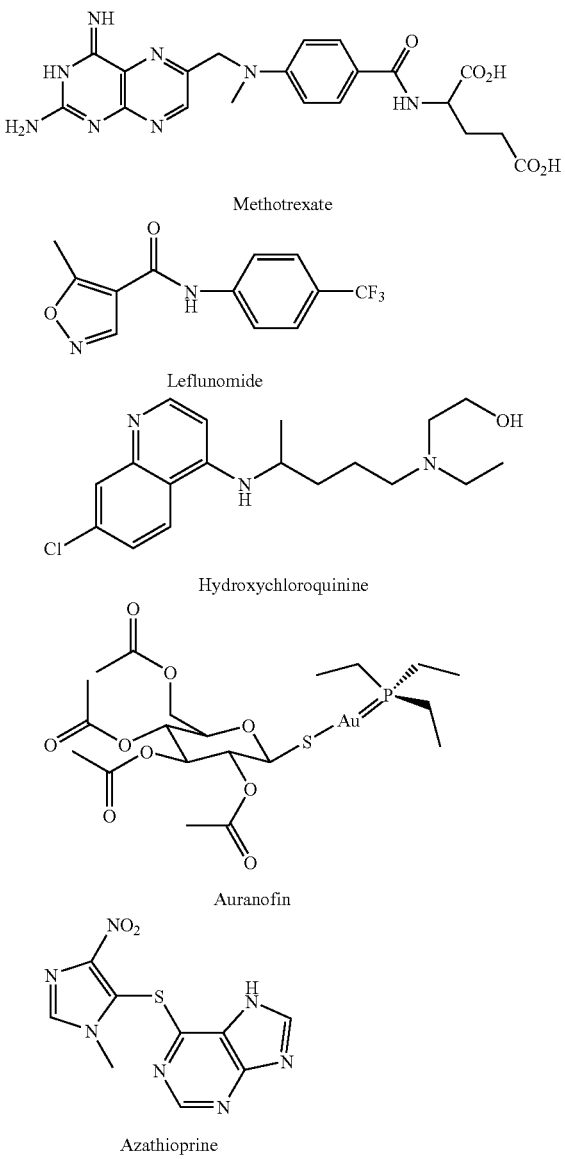

Methotrexate

Leflunomide

Hydroxychloroquinine

Auranofin

Azathioprine

Methotrexate is one DMARD that is commonly prescribed. The precise mechanisms of action of methotrexate have not been fully elucidated, but are thought to include direct promotion of synovial cell apoptosis, blocking the proliferation of lymphocytes, reducing production of interleukin 1 and induction of adenosine release leading to immunosuppression. Despite its efficacy, its toxicity profile is not optimal and its pharmokinetic properties are rather unsatisfactory: more than 80% undergoes fast elimination unchanged after uptake. Further, around 35% of patients do not respond sufficiently well to treatment with methotrexate alone.

Leflunomide is a relatively new DMARD that inhibits dihydroorotate dehydrogenase, an enzyme involved in de novo pyrimidine synthesis. It works more quickly than methotrexate but is more likely to cause side effects. For instance, serious liver injuries have been reported in patients taking this drug, some with a fatal outcome.

There are other drugs that cause fewer side effects but are less potent, such as auranofin and hydroxychloroquine. Other DMARDs are reserved for severe RA since they are very effective but cause serious side effects; such drugs include azathioprine, ciclosporin and cyclophosphamide.

Cytokine inhibitors have also been used to some effect in the treatment of RA. For instance, inhibitors of tumour necrosis factor α such as etanercept and infliximab have been administered by injection or drip, whereas inhibitors of interleukin-1 such as anakinra are sometimes combined with methotrexate therapy when the latter is ineffective alone.

Research has identified genes that may contribute to rheumatoid arthritis and may also be implicated in several other autoimmune/inflammatory diseases (Kawahito et. al., *Journal of Immunology*, 1998, 161: 4411-4419). Indeed, some of the above drugs have additionally been found to be effective in the treatment of such diseases. For instance, hydroxychloroquinine can be used to treat systemic lupus erythematosus, whereas both methotrexate and leflunomide can be prescribed for psoriatic arthritis. Ciclosporin has been found useful in treating severe psoriasis or eczema, azathioprine relieves auto-immune haemolytic anaemia and auto-immune chronic active hepatitis, and infliximab can treat Crohn's disease, ulcerative colitis and ankylosing spondylitis. Azathioprine and ciclosporin are also immunosuppressant drugs that can be used to prevent the body's rejection of an organ transplant.

In light of the foregoing, there remains a need for alternative immunosuppressant drugs and alternative therapies for rheumatoid arthritis and related diseases that may address one or more of the aforementioned problems.

Accordingly, in a first aspect of the invention, there is provided the use of a compound of the formula I, or a pharmaceutically acceptable salt thereof, for the manufacture of a medicament for use in modulating an immune or inflammatory response:

I

A—B—⟨benzene ring⟩—C(=Z)—$(CH_2)_n$—$\overset{*}{C}HR^4$,
                                        |
                                        $R^3$ wherein:
Z=O or S;
n=1-3;
$R^3$=—$CO_2R^8$, —$C(O)SR^8$, —$C(O)NHR^8$, —$C(S)OR^8$, —$C(S)SR^8$, —$C(S)NHR^8$, —$C(NH)SR^8$ or —$C(NH)NHR^8$,
  wherein $R^8$ is —H or alkyl;
$R^4$=—H, —$CH_2R^5$ or —$CH_2CH_2R^5$,
  wherein $R^5$ independently has one of the meanings of $R^3$;
B=—$NR^2$—, —$CH_2NR^2$—, —$CH_2CH_2NR^2$—, —$CH_2CHR^7$— or —$CH_2O$—,
  wherein $R^2$ is H or a $C_{1-3}$ alkyl, alkenyl or alkynyl group, and
  $R^7$ is H or a $C_{1-3}$ alkyl or alkoxy group;

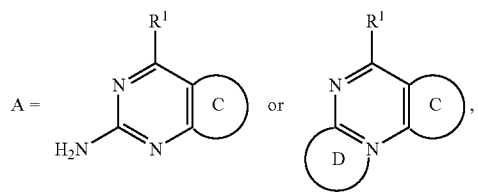

wherein $R^1$=—$NH_2$ or —OH,
  C and D are each, independently, a 5- or 6-membered, substituted or unsubstituted, aromatic or non-aromatic ring which may also contain one or more heteroatoms, and C is connected to group B in any available position.

Preferred embodiments of the invention are as described below or as defined in the sub-claims.

Figure 1:
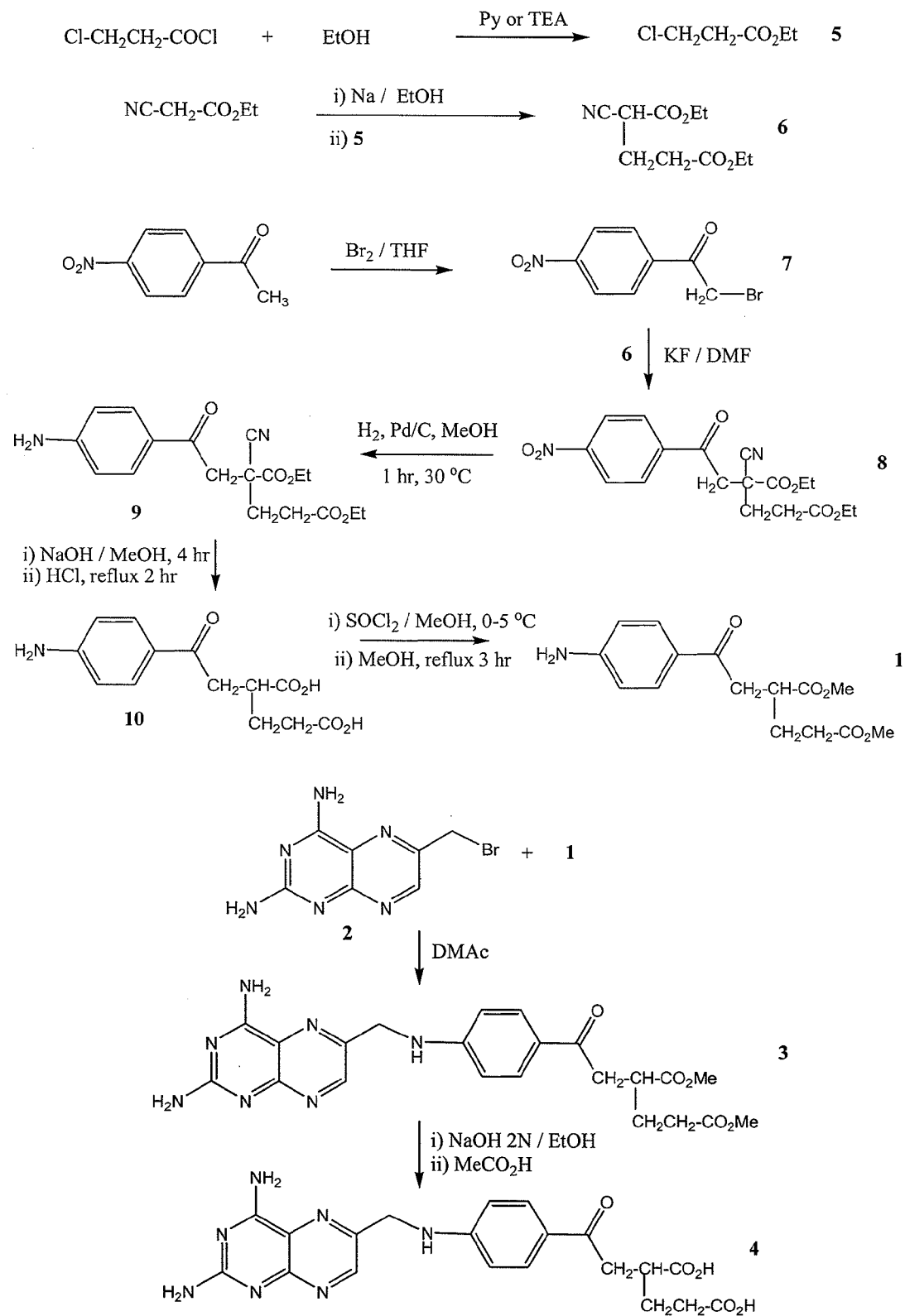
FIG. 1 is a schematic representation of the total synthesis of two compounds used in the present invention (compounds 3 and 4), as described in detail below in Examples 1 and 2.

In formula I, the carbon marked C* may be asymmetric (when $R^4$ is not H) and in this event it will be appreciated that compounds of the formula I may exist in racemic form, or may be separated into their (+) or (−) enantiomers by conventional methods. In addition, other chiral centres may be present in some compounds giving rise to one or more further pairs of enantiomers. For example, a second chiral centre exists in those compounds wherein B=—$CH_2CHR^7$— wherein $R^7$ is a $C_{1-3}$ alkyl or alkoxy group. Use of all such racemic or enantiomeric forms are intended to lie within the scope of the present invention. Furthermore, it will be understood that the compounds of formula I may exist in one or more tautomeric forms, and use of each of these forms are also intended to lie within the scope of the present invention.

It is preferred to use compounds of the formula I in which one or more of the following conditions are satisfied:
Z is O;
n is 1;
$R^3$ is —$CO_2R^8$ and $R^4$ is —$CH_2CH_2CO_2R^8$;
$R^8$ is —H, methyl, ethyl, n-propyl, isopropyl, n-butyl, isobutyl or tertiary butyl, preferably —H, -Me or -Et, preferably —H;
B is —$CH_2NR^2$—, —$CH_2CHR^7$— or —$CH_2O$—, preferably —$CH_2NR^2$—;
$R^2$ is —H, -Me, -Et or —$CH_2$—C≡CH, preferably H;
$R^7$ is -Me, -Et or —OMe, preferably H.

In addition, preferred compounds of the formula III, V or VII display one or more of the preferred designations of Z, n, $R^2$, $R^3$, $R^4$ and/or $R^7$ set out above.

In group A in formulae I, II, IV or VI, D is preferably a 5-membered heteroaromatic ring. Preferably, A is

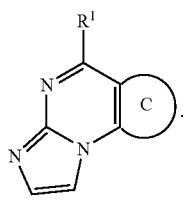

In group A, C may be one of the following groups (points of attachment to the adjacent ring and to group B are shown):

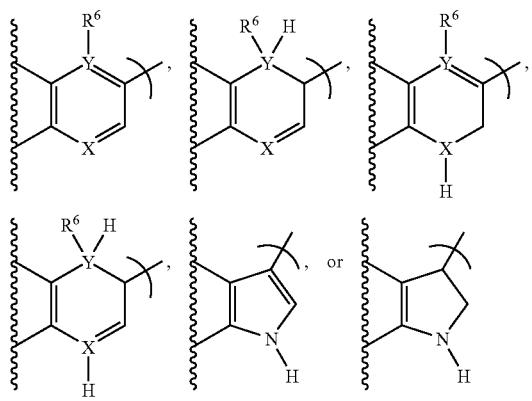

wherein X is CH or N, and either: Y is C and $R^6$ is H, Me, Et or HCO; or Y is N and $R^6$ is a lone pair of electrons. In preferred embodiments, X and Y are both N and $R^6$ is a lone pair of electrons.

Especially preferred A groups are those of the following structures:

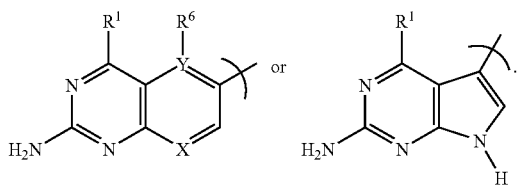

Of particular interest are the following two A groups:

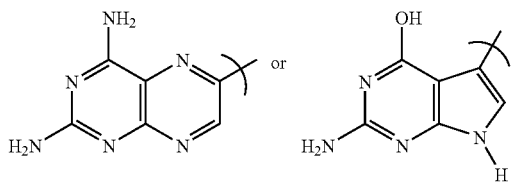

Especially preferred are compounds of the formula I having the above two A groups, wherein B is —CH$_2$NR$^2$—, $R^2$ is —H, -Me, -Et or —CH$_2$C≡CH, Z is O, n is 1, and $R^3$ is —CO$_2$R$^8$, preferably any hydrolysable ester group. Individual examples of this group of compounds are set out below.

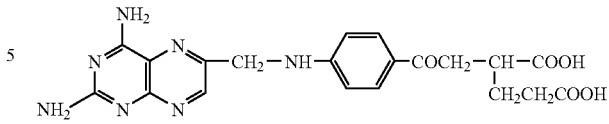

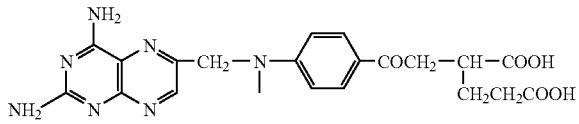

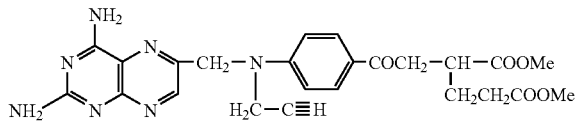

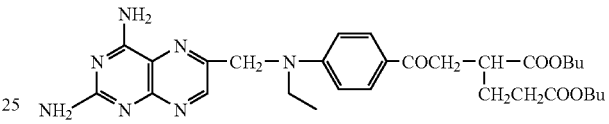

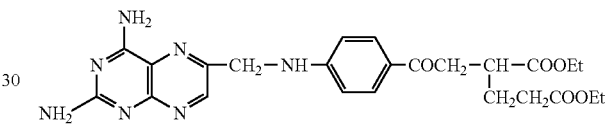

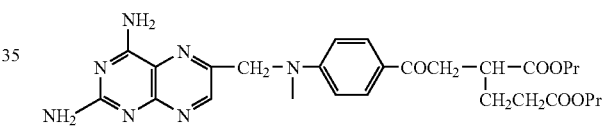

Compounds of the formula I can be synthesized by a variety of methods from readily available and inexpensive starting materials. For instance, in the case where B is —NR$^2$—, —CH$_2$NR$^2$— or —CH$_2$CH$_2$NR$^2$—, a compound of the formula II A-(CH$_2$)$_m$—X          II wherein A is as previously defined, m is 0, 1 or 2 and X is a leaving group, can be reacted with a compound of the formula III

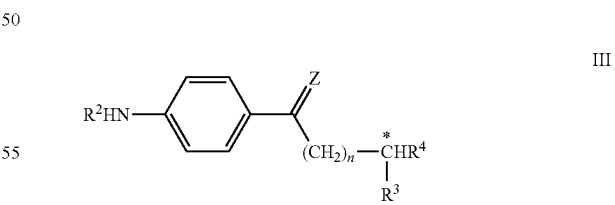

wherein Z, n, $R^2$, $R^3$ and $R^4$ are as previously defined. The leaving group X will generally be a halogen such as chlorine, bromine or iodine, especially bromine or iodine. This reaction is preferably performed in a dipolar aprotic solvent such as dimethyl formamide (DMF) or dimethylacetamide (DMAc). A basic catalyst such as potassium fluoride may be used, which affords a higher yield than tertiary amines or sodium bicarbonate. Where necessary, sensitive groups may be protected prior to the reaction using suitable protecting groups known in the art, and later deprotected via standard methods. For example, when $R^3$ is H and $R^4$ is $CH_2CH_2CO_2H$, these acid groups may be protected for instance as methyl ester groups, with subsequent deprotection by known methods such as alkaline hydrolysis with sodium hydroxide in ethanol and precipitation by addition of acid, such as glacial acetic acid.

In the case where B is —$CH_2O$—, the compounds of formula I may be prepared, for example, by coupling a compound of the formula IV

   IV wherein A is as previously defined and X is a leaving group, with a compound of the formula V

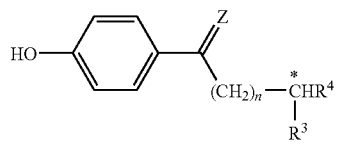   V wherein Z, n, $R^3$ and $R^4$ are as previously defined, by a Williamson ether type reaction. In this reaction, the compound of formula V is generally converted into its aroxide ion form prior to reaction with the compound of formula IV, using a base such as NaH, for instance. X may be any suitable leaving group, in particular a halide.

In the case where B is —$CH_2CHR^7$—, the compound of formula I may be prepared, for example, by coupling a compound of the formula VI with a compound of the formula VII

VI
VII

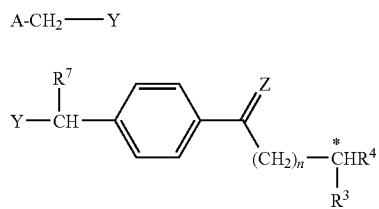

wherein A, Z, n, $R^3$, $R^4$, and $R^7$ are as previously defined, and Y is, in each case independently, a halide, by any known carbon-carbon bond forming reaction, especially those involving the use or formation of organometallic reagents such as Grignard reagents and lithium or copper-lithium compounds. For instance, a compound of the formula VII may be converted into its corresponding Grignard reagent or lithium cuprate reagent and reacted with a compound of the formula VI. Alternatively, a compound of the formula VI may be converted into its corresponding Grignard reagent or lithium cuprate reagent and reacted with a compound of the formula VII. Once again, suitable protecting groups for any reactive substituent groups will be well-known to those skilled in the art.

The intermediates II to VII may be prepared by conventional methods. By way of illustration, compounds of the formula III, V or VII may be prepared by reacting a compound of the formula

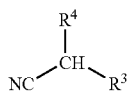

with a compound of the formula

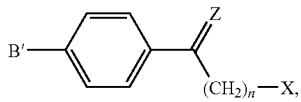

wherein B' is —$NHR^2$, —OH or —$CHYR^7$ and X is a leaving group, in the presence of a base. This may be followed by removal of the cyano group by hydrolysis and decarboxylation, with the use of suitable protecting groups where necessary.

Although not wishing to be limited by theory, it is believed that the modified ketomethylenic or thioketomethylenic side chain of the compounds of formula I leads to a lower renal toxicity compared with methotrexate. Inactivation due to hydrolysis is minimal due to the lower lability of the ketomethylenic or thioketomethylenic group, allowing a longer half-life. In addition, compounds of the formula I exhibit improved physico-chemical characteristics compared with those of the prior art.

As discussed above, primary interest is in the use of compounds of the formula I in the treatment of inflammatory diseases such as rheumatoid arthritis. The therapeutic utility of these compounds extends further, however, to the modulation of an immune and/or inflammatory response in general, such as in immunosuppressive therapy. Immunosuppression may be an adverse effect of certain diseases such as AIDS. However, immunosuppressive therapy refers to the deliberate induction of immunosuppression for a therapeutic purpose, such as for the treatment or prevention of an autoimmune disease or for preventing rejection of an organ transplant. Immunosuppressive therapy may involve, for instance, inhibition of cytokine production, especially tumour necrosis factor α, interleukin-4 or -13, or interferon-γ.

Examples of other autoimmune and inflammatory diseases treatable in this invention are: arthritic diseases such as psoriatic arthritis, juvenile idiopathic arthritis and ankylosing spondylitis; inflammatory muscle diseases such as dermatomyositis and polymyositis; diseases involving inflammation of other tissues such as neuronal tissue and the inner ear; skin diseases such as psoriasis, eczema, pemphigus vulgaris and chronic refractory idiopathic thrombocytopenic purpura; inflammatory bowel diseases such as Crohn's disease and ulcerative colitis; vasculitis e.g. polyarteritis nodosa; auto-immune haemolytic anaemia such as systemic lupus erythematosus; auto-immune hepatitis; neurodegenerative autoimmune diseases such as multiple sclerosis; pericarditis; bronchial asthma or atopy; type 1 diabetes; uveitis; thyroiditis; and scleroderma.

Preferably the compounds of the formula I are used to treat any of the following diseases: psoriatic arthritis, juvenile idiopathic arthritis, ankylosing spondylitis, dermatomyositis, polymyositis, psoriasis, eczema, pemphigus vulgaris, chronic refractory idiopathic thrombocytopenic purpura, Crohn's disease, ulcerative colitis, polyarteritis nodosa, auto-immune haemolytic anaemia, auto-immune hepatitis, or inflammation of the neuronal tissue or inner ear.

In another embodiment, compounds of the formula I are used to prevent rejection of an organ transplant.

A preferred use of the compounds of formula I is to treat rheumatic diseases, especially arthritic diseases, very preferably rheumatoid arthritis, psoriatic arthritis, juvenile idiopathic arthritis or ankylosing spondylitis.

The compounds may be administered by any suitable mode of administration, preferably orally (in solid, e.g. tablet, or liquid form) or parenterally, or via topical applications. They may be given alone or in combination with other therapeutic agents, such as other biological agents, antirheumatic agents, other immunosuppressants or immunomodulators such as monoclonal antibodies, to a mammal, preferably a human. They may also be administered with adjuvants such as folate derivatives, folic acid or folinic acid.

The following examples are intended to demonstrate the invention but are not intended to limit the invention in any manner.

EXAMPLE 1

Synthesis of Compound 3

Source of Starting Materials 3-chloropropanoyl chloride and ethyl cyanoacetate were obtained commercially from Sigma-Aldrich Company Ltd., The Old Brickyard, New Road, Gillingham, Dorset SP8 4XT, United Kingdom, or synthesised by standard methods. α-bromo-p-nitro-acetophenone 7 was obtained by bromination of p-nitroacetophenone with bromine in tetrahydrofuran (THF). 2,4-diamino-6-bromomethylpteridine 2 was obtained by standard methods (see, for example, U.S. Pat. No. 4,077,957 and U.S. Pat. No. 4,224,446).

Step A:
Synthesis of Compound 6

3-chloropropanoyl chloride was esterified with ethanol in the presence of pyridine or triethylacetate to produce ethyl 3-chloropropionate 5. The latter was condensed with ethyl cyanoacetate according to the procedure of L. Ruzicka et. al., *Helv. Chim. Acta* 17, 183-200 (1934), CA 28:2584, or Koelsch, C. F., *J. Am. Chem.* 65, 2458-9 (1943), to form diethyl α-cyanoglutarate 6. $^1$H-NMR confirmed the expected structure. GC: 97% purity.

Step B:
Synthesis of Compound 8

175 g (0.71 mmol) α-bromo-p-nitro-acetophenone 7 was added in portions at 0-5° C. to a suspension of 175 g (0.82 mmol) diethyl α-cyanoglutarate 6 and 175 g (3 mmol) KF in 500 ml DMF. The reaction was monitored by thin layer chromatography (TLC). After 4 hours, the reaction mixture was suspended in 2 l of water containing 0.1% acetic acid at pH 5. After decanting the water, the gummy precipitate was washed with water (2×750 ml) then triturated with 300 ml methanol. When crystallisation was complete, the precipitate was filtered and washed successively with an excess of methanol and ether, affording 210 g of compound 8, a yellow solid with m.p. 92.1° C. (Yield 68%) After chromatography on silica gel (50:50:5 benzene-cyclohexane-ethanol) the product had m.p. 99.7° C. TLC on silica gel plates (5:1:3:10:0.1 benzene-ethanol-cyclohexane-petroleum ether-AcOH) showed a single spot with Rf (retention factor) 0.38. HPLC: 97% purity.

Step C:
Synthesis of Compound 9

30 g (0.08 mmol) compound 8 was dissolved in 400 ml methanol and hydrogenated in a hydrogenation flask at room temperature in the presence of 6 g 20% Pd/C catalyst. The theoretical volume of hydrogen (c. 6200 ml; 0.28 mmol) was absorbed in 1 hour (TLC control). The platinum catalyst was filtered and the methanol was evaporated. The crude product obtained solidified on drying in vacuo, resulting in 27.6 g compound 9, a yellow solid (yield 99%) which was used without further purification in the conversion to crude compound 10 described below. The purity was acceptable by TLC analysis. TLC (4:1 chloroform-methanol) showed a single spot, Rf 0.5 (characteristic reaction with 4-dimethylamino benzaldehyde). The HCl salt was isolated after reflux in HCl. LC-MS and $^1$-H NMR confirmed the expected structure; HPLC: 99% purity.

Step D:
Synthesis of Compound 10

A solution of 52.2 g (0.15 mmol) intermediate 9 in 1000 ml methanol was prepared. 188 ml 6N NaOH was added dropwise at room temperature for 1 hour and the solution was allowed to stand for 12 hours. The reaction mixture was then diluted with 300 ml water and concentrated under high vacuum. 700 ml 37% HCl was added to the residue and the resulting mixture was heated to reflux for 4 hours.

The mixture obtained was diluted with 1.5 l methanol and the NaCl precipitate was removed by filtration. The filtrate was used in step E. A small amount of diacid 10 was isolated before dilution, by filtering the suspension and washing the precipitate successively with an excess of water, acetone and ether. TLC (4:1 chloroform-methanol) showed a single spot, Rf 0.26.

Step E:
Synthesis of Compound 1

The methanolic solution of the dicarboxylic acid 10 obtained in step D was cooled at 0-5° C. and 100 ml thionyl chloride was added dropwise. The reaction mixture was stirred under reflux for 3 hours, then cooled to room temperature and the solvent was evaporated off. The precipitate obtained was filtered and washed with ether, resulting in 27 g compound 1 (yield 63%), a solid with m.p. 115-116° C. After recrystallisation from tetrahydrofuran, 17.5 g white crystals of 1 were obtained having m.p. 116-117° C. TLC (4:1 chloroform-methanol) showed a single spot, Rf 0.73. UV spectra: 234, 319 nm (MeOH). $^1$H NMR spectra: 2.0 (2H, m, C$\underline{H_2}$CH$_2$COOCH$_3$), 2.5 (2H, t, CH$_2$C$\underline{H_2}$COOCH$_3$), 3.1 (2H, $\underline{m}$, COCH$_2$), 3.5 (1H, m, COCH$_2$C$\underline{H}$), 3.75 (6H, s, COOC$\underline{H_3}$), 7.6-8.0 (4H, m, C$\underline{H}$ arom.). HPLC: 99% purity.

Step F:

Synthesis of N-[4-[[2,4-diamino-6-pteridinyl)methyl]amino]benzoyl]pseudoglutamic ester (Compound 3)

A mixture of 7 g (27.4 mmol) 2,4-diamino-6-bromomethylpteridine 2 and 7 g (23.4 mmol) dimethyl N-[4-methylamino)benzoyl]pseudogluamate 1 in 70 ml N,N-dimethylacetamide was stirred for 30 minutes at 70° C. then allowed to stand at room temperature overnight protected from light, then heated again for 10 minutes to 100° C. The reaction was controlled by TLC. After cooling, the reaction mixture was poured into water acidified with AcOH at pH 4 (1000 ml). The dark-yellow precipitate that formed was filtered and washed three times with water and allowed to air dry. 2.6 g orange-yellow product 3 was obtained, m.p. 200-210° C. The filtrate was treated with 10% NaHCO$_3$ and the precipitate formed was separated in the same manner, resulting in a second fraction of dimethyl ester 3 (2 g). Total yield: 36%. TLC (4:1 chloroform-methanol) showed a single spot, Rf 0.48. UV Spectra: 210, 242, 332 (0.1 N HCl); 238, 335 (MeOH).

EXAMPLE 2

Synthesis of N-[4-[[2,4-diamino-6-pteridinyl)methyl]amino]benzoyl]pseudoglutamic acid (Compound 4)

1 g (2.1 mmol) dimethyl ester 3 was added in portions to a solution of 10 ml 2N NaOH and 25 ml ethanol, and the mixture was stirred at room temperature for 4 hours. The precipitate formed was filtered and dissolved in distilled water. The alkaline solution was treated with charcoal, filtered and the pH was adjusted to 4.5 with 10% AcOH. The precipitate was filtered and washed with water at pH 4.5, then with acetone, resulting in 0.8 g compound 4 (yield 85%). The product, a brown solid, was purified by preparative HPTLC (High Performance Thin Layer Chromatography). After elution with 50:50:5 $CH_3CN$—$H_2O$—$NH_4OH$, the diacid was extracted from silica gel with 100 nil NaOH solution at pH 8. The water was removed by freeze-drying. TLC (7:2:1 $CH_3CN$—$H_2O$—$NH_4OH$) showed a single spot, Rf 0.80. Mass spectrum: m/z 120 (M+, 100%). IR spectra (KBr): 1651 ($COCH_2$), 1594 (C=C), 1563, 1403 (CO=acid), 1176 (C=O), 823 (CH). UV spectra: 242, 332 nm (0.1 N HCl); 232, 259, 325 nm (0.1 N NaOH); 229, 262, 318 (MeOH). $^1H$ NMR: 1.6 (3H, m, CH—$CH_2$), 2.2 (2H, t, $CH_2CH_2COOH$), 2.9 (2H, m, $COCH_2$), 4.6 (2H, s, $CH_2NH$), 6.8-7.8 (4H, m, C H arom.), 9 (1H, s, 7-CH). HPLC: 97% purity.

Other compounds of formula I can be produced by adapting the procedures set out above in an appropriate manner. For example, intermediate 1 and analogous compounds can be converted to their corresponding N-methyl derivatives by reaction with formaldehyde and sodium cyanoborohydride. Intermediate 6 can also be produced by reacting ethyl cyanoacetate with ethyl acrylate according to standard procedures.

EXAMPLE 3

Treatment of RA in Mice In Vivo

The Collagen-Induced RA (CIA) Model

The ability of compounds of formula I to treat collagen-induced rheumatoid arthritis in mice was examined. The CIA model is one thought to involve both cellular and humoral immunity.

RA Induction

DBA/1 male mice, 7-8 weeks old (Harlan, UK) were housed in groups of 10 with free access to food and water. One volume of bovine type II collagen (2 mg/ml solution in 0.05 M acetic acid) was emulsified with an equal volume of Complete Freund's Adjuvant (CFA; *Mycobacterium tuberculosis* 4 mg/ml). All the mice were immunised on day 0 by intradermal injection into their tails of 0.1 ml of this emulsion (100 μg collagen per mouse), under Halothane anesthesia, using a plastic syringe. Location of the injection was at an approximate caudal distance of 1 cm from the base of the tail. The mice were also presented with a collagen challenge by intraperitoneal injection (200 μg bovine type II collagen per mouse in phosphate buffered saline, PBS) on day 21.

Treatment

Vehicle alone was used as negative control, whereas methotrexate (MTX) in PBS was used as a positive control. The acidic compound of formula I-A1 was dissolved in 0.2 N NaOH to afford a 50 mg/ml stock solution and then diluted in PBS to give a range of concentrations. Other compounds of formula I were dissolved in a similar manner. Each of the groups of 10 mice were given 5 ml/kg of a test or control fluid by intraperitoneal injection, once daily from day 0 for 6 weeks.

Observations and Examinations

Mice were examined for signs of arthritogenic responses in peripheral joints on day 17 and thereafter once daily until termination of the study. Arthritis reactions were reported for each paw according to a 0-4 scale in ascending order of severity as described below, and a total arthritis score per mouse was calculated. Paw thickness was measured in mm in both hind paws (left & right, just below the foot pad and above the calcaneum) of each animal. Measurements were made on day 17 and thereafter once daily until termination of the study using a dial caliper (Kroeplin, Munich, Germany).

| Arthritis Score | Grade |
|---|---|
| No reaction, normal | 0 |
| Mild, but definite redness and swelling of the ankle/wrist or apparent redness and swelling limited to individual digits, regardless of the number of affected digits | 1 |
| Moderate to severe redness and swelling of the ankle/wrist | 2 |
| Redness and swelling of the entire paw including digits | 3 |
| Maximally inflamed limb with involvement of multiple joints | 4 |

On day 0, 17 and thereafter once daily, careful clinical examinations were carried out and recorded. Observations included changes in skin, fur, eyes, mucous membranes, occurrence of secretions and excretions (e.g. diarrhea) and autonomic activity (e.g. lacrimation, salivation, piloerection, pupil size, unusual respiratory pattern). Changes in gait, posture and response to handling, as well as the presence of bizarre behavior, tremors, convulsions, sleep and coma were also noted.

Individual body weights of animals were monitored during the experiment. The study was terminated on day 42.

Results

Figure 2:
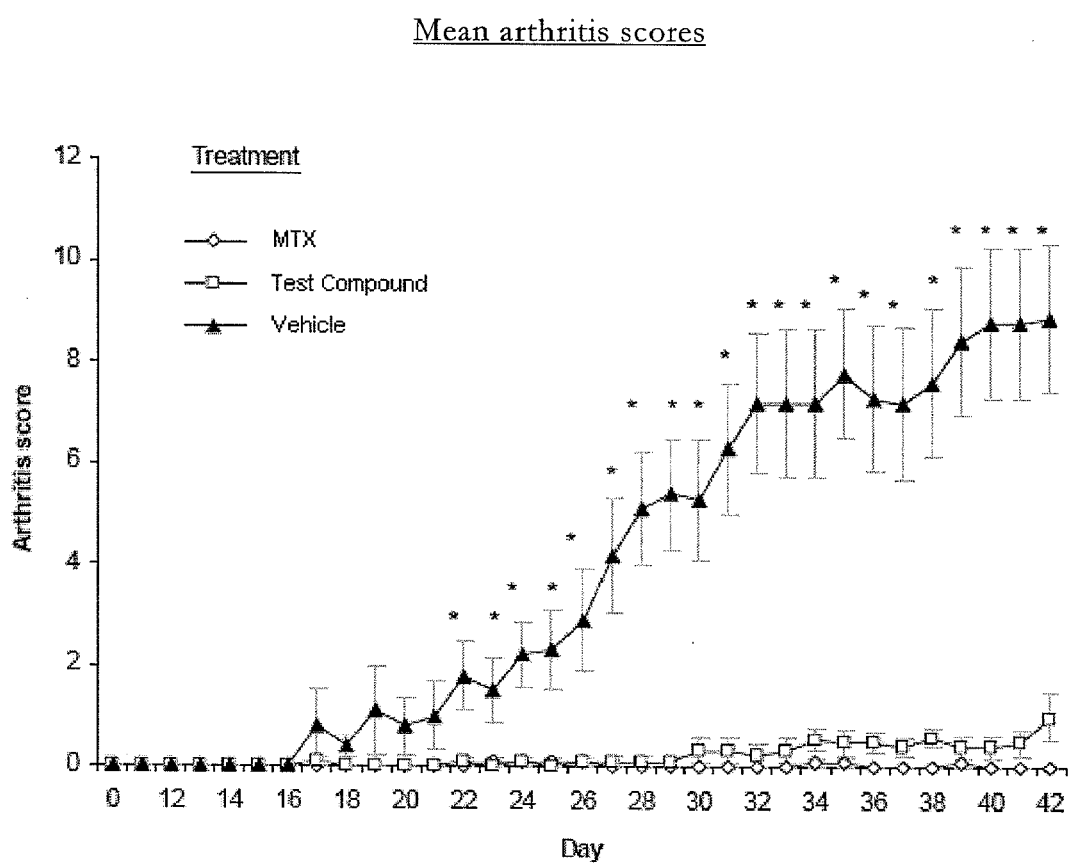
FIG. 2 shows the mean arthritis scores of mice treated with compound I-A1 during a collagen-induced arthritis study.

The results showed that compounds of formula I exerted significant anti-arthritic effects in this model. Mice being treated with the negative (vehicle) control had significantly higher arthritis scores and greater hind paw thickness than did mice being treated with the test compounds (see FIG. 2). In addition, the anti-arthritic effects of the test compounds were correlated with significantly reduced histology scores in the limbs (synovial hyperplasia, reduced bone/cartilage erosion and cell infiltrate).

In comparison with methotrexate, the compounds were tolerated at higher absolute doses and were effective at a lower percentage of the maximum tolerated dose. For instance, the compound of formula I-A1 was effective at a therapeutic dose of 10% of maximum tolerated dose whereas methotrexate required a therapeutic dose twice as high.

Figure 3:
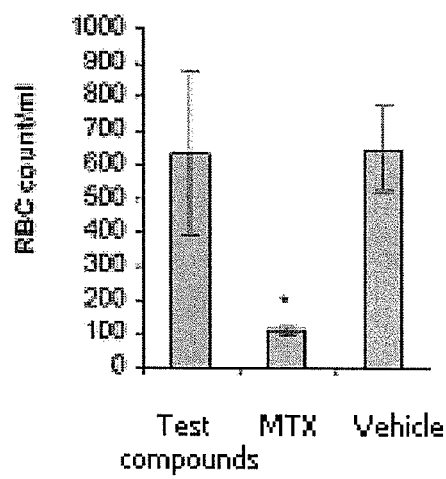
FIG. 3 shows mean red blood cell counts at the end of the study, for mice treated with test compounds, methotrexate (positive control) and vehicle alone (negative control).

With regard to other clinical symptoms examined at the end of the study, the groups treated with compounds of formula I showed a marked improvement over the corresponding methotrexate-treated groups. For instance, mice treated with methotrexate presented severe signs of anaemia at the end of the study, but this was completely absent from the groups treated with test compounds. Measurements of red blood cell count confirmed this, as shown in FIG. 3. No other side-effects were observed during the treatment, suggesting that the test compounds were well tolerated.

EXAMPLE 4

Treatment of RA in Rats In Vivo

The Adjuvant-Induced RA (AIA) Model

The ability of compounds of formula I to treat adjuvant-induced rheumatoid arthritis in rats was examined. The AIA model is one thought mainly to involve T cell-mediated mechanisms.

RA Induction

Male Lewis rats weighing 200±10 g were housed in groups of 6 with free access to food and water. 0.1 ml CFA (*Mycobacterium tuberculosis* 3 mg/ml) was injected into the subplantar region of the right hind paw of each rat on day 1 of the study.

Treatment

Test substances were first dissolved in NaOH (if required) as explained above then suspended in 2% Tween 80 to a range of concentrations. 10 ml/kg was administered by oral gavage for 21 consecutive days, beginning (on day 1) 1 hour before injection of CFA. 2% Tween 80 was used as a negative control and methotrexate in 2% Tween 80 as a positive control.

Observations and Examinations

Right hind paw volumes were measured by water displacement on day 0, 4 hours after the CFA injection on day 1, and on days 7, 14, and 21. Left hind paw volumes were measured by water displacement on days 0, 1, 7, 14, and 21. Cumulative increases in paw volume were calculated, and compared with that observed for the vehicle-treated control. 30% or more reduction in paw volume relative to the negative control was considered significant anti-inflammatory activity. Body weight was also recorded on days 1, 7, 14, and 21. Symptoms of swelling in the front paws, tail, nose and ears were recorded on day 21.

Results

General symptoms of polyarthritis: 100% of the negative control rats developed polyarthritis, whereas no treated animals developed these symptoms. No significant change in body weight was observed for the rats treated with the lower doses of test compounds versus the negative control-treated group. Mean hind paw volumes of representative groups tested are reported below.

Group 1—Negative control (vehicle alone); Group 2—MTX control; Group 3—compound of formula I-A1 (low dose)

| Acute phase: swelling in CFA treated paw | | | | | | | | |
|---|---|---|---|---|---|---|---|---|
| | Mean right hind paw volume (ml water displaced) Day | | | | | % Inhibition of swelling in each time interval relative to negative control | | |
| Group | 0 | 1 | 7 | 14 | 21 | 0-1 | 0-7 | 0-14 | 0-21 |
| 1 | 1.06 | 1.66 | 2.17 | 2.63 | 2.93 | 0 | 0 | 0 | 0 |
| 2 | 1.06 | 1.56 | 1.79 | 1.48 | 1.37 | 15 | 34 | 73 | 83 |
| 3 | 1.05 | 1.63 | 1.99 | 1.68 | 1.50 | 3 | 15 | 60 | 76 |

| Delayed phase: swelling in CFA untreated paw | | | | | | | | |
|---|---|---|---|---|---|---|---|---|
| | Mean left hind paw volume (ml water displaced) Day | | | | | % Inhibition of swelling in each time interval relative to negative control | | |
| Group | 0 | 1 | 7 | 14 | 21 | 0-1 | 0-7 | 0-14 | 0-21 |
| 1 | 1.07 | 1.07 | 1.08 | 1.91 | 2.46 | 0 | 0 | 0 | 0 |
| 2 | 1.06 | 1.06 | 1.08 | 1.10 | 1.14 | — | — | 95 | 94 |
| 3 | 1.05 | 1.05 | 1.06 | 1.09 | 1.11 | — | — | 95 | 95 |

It is concluded that compounds of formula I are highly active against both acute and late phase of the Complete Freund's Adjuvant (CFA)-induced arthritis in rats.

Results from these two studies demonstrated that administration of compounds of formula I inhibits disease development and severity in animal models of arthritis using multiple clinical measures.

The invention claimed is:

1. A method, comprising: treating rheumatoid arthritis, in a subject in need thereof by administering, to the subject, a compound of formula I, or a pharmaceutically acceptable salt thereof:

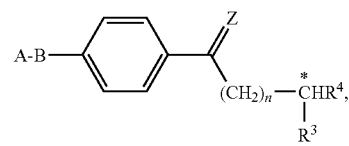

I wherein:
Z=O or S;
n=1-3;
$R^3$=—$CO_2R^8$, —C(O)$SR^8$, —C(O)$NHR^8$, —C(S)$OR^8$, —C(S)$SR^8$, —C(S)$NHR^8$, —C(NH)$SR^8$ or —C(NH)$NHR^8$,
wherein $R^8$ is —H or alkyl;
$R^4$=—H, —$CH_2R^5$ or —$CH_2CH_2R^5$,
wherein $R^5$ independently has one of the meanings of $R^3$;
B=—$NR^2$—, —$CH_2NR^2$—, —$CH_2CH_2NR^2$—, —$CH_2CHR^7$— or —$CH_2O$—,
wherein $R^2$ is H or a $C_{1-3}$ alkyl, alkenyl or alkynyl group, and
$R^7$ is H or a $C_{1-3}$ alkyl or alkoxy group;
A=

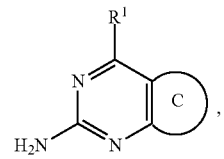

wherein:
$R^1$=—$NH_2$ or —OH,
C is a 5- or 6-membered, substituted or unsubstituted, aromatic or non-aromatic ring which optionally contains one or more heteroatoms, and C is connected to group B in any available position.

2. A method as claimed in claim 1, wherein Z is O.

3. A method as claimed in claim 1, wherein n is 1.

4. A method as claimed in claim 1, wherein $R^8$ is —H, methyl, ethyl, n-propyl, isopropyl, n-butyl, isobutyl or tertiary butyl.

5. A method as claimed in claim 1, wherein $R^3$ is —$CO_2R^8$ and $R^4$ is —$CH_2CH_2CO_2R^8$.

6. A method as claimed in claim 5, wherein $R^8$ is H, methyl or ethyl.

7. A method as claimed in claim 1, wherein B is —$CH_2NR^2$—, —$CH_2CHR^7$— or —$CH_2O$—.

8. A method as claimed in claim 7, wherein B is —$CH_2NR^2$—.

9. A method as claimed in claim 1, wherein $R^2$ is —H, -Me, -Et or —$CH_2$≡CH.

10. A method as claimed in claim 1, wherein $R^7$ is —H, -Me, -Et or —OMe.

11. A method as claimed in claim 1, wherein C is:

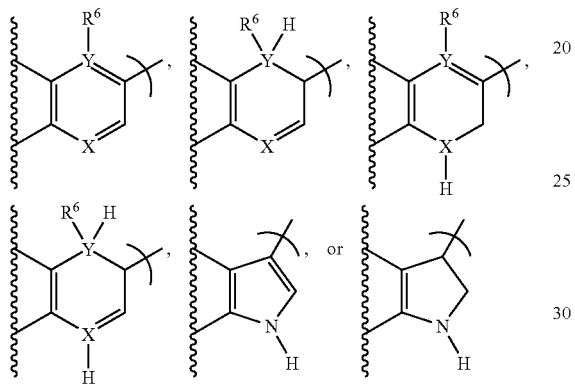

wherein X is CH or N, and either:
  Y is C and $R^6$ is H, Me, Et or HCO; or
  Y is N and $R^6$ is a lone pair of electrons.

12. A method as claimed in claim 1, wherein A is of the formula A-i or A-ii:

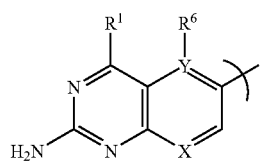

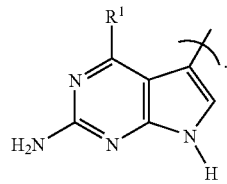

13. A method as claimed in claim 12, wherein A is of the formula A-i-1 or A-ii-1:

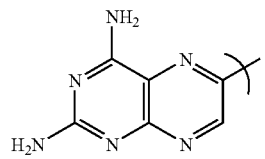

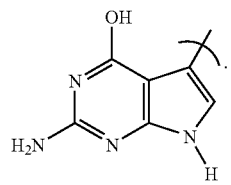

14. A method as claimed in claim 13, wherein B is —$CH_2NR^2$—; $R^2$ is —H, -Me, -Et or —$CH_2C$≡H; Z is O; n is 1; and $R^3$ is —$CO_2R^8$.

15. A method as claimed in claim 13, wherein B is —$CH_2NR^2$—, —$CH_2CH_2$—, —$CH_2CHCH_3$— or —$CH_2O$—; $R^2$ is —H, -Me, -Et or —$CH_2C$≡CH; Z is O; n is 1; $R^3$ is —$CO_2R^8$; $R^4$ is —H or —$CH_2CH_2CO_2R^8$; $R^8$ is independently —H, -Me or -Et; if A is A-i and Y is C, $R^6$ is —H; and if A is A-ii, $R^1$ is —OH.

* * * * *

UNITED STATES PATENT AND TRADEMARK OFFICE
CERTIFICATE OF CORRECTION

| | | |
|---|---|---|
| PATENT NO. | : 8,247,422 B2 | |
| APPLICATION NO. | : 12/449448 | |
| DATED | : August 21, 2012 | |
| INVENTOR(S) | : Dan Stoicescu | |

It is certified that error appears in the above-identified patent and that said Letters Patent is hereby corrected as shown below:

At column 15, claim 9, line 13, please change "–$CH_2{\equiv}CH$" to "$CH_2C{\equiv}CH$".

At column 16, claim 14, line 35, please change "–$CH_2C{\equiv}H$" to "–$CH_2C{\equiv}CH$".

Signed and Sealed this
Sixteenth Day of October, 2012

David J. Kappos
*Director of the United States Patent and Trademark Office*

UNITED STATES PATENT AND TRADEMARK OFFICE
CERTIFICATE OF CORRECTION

PATENT NO. : 8,247,422 B2
APPLICATION NO. : 12/449448
DATED : August 21, 2012
INVENTOR(S) : Dan Stoicescu Page 1 of 1

It is certified that error appears in the above-identified patent and that said Letters Patent is hereby corrected as shown below:

At column 15, claim 9, line 13, please change "–$CH_2{\equiv}CH$" to "–$CH_2C{\equiv}CH$".

At column 16, claim 14, line 35, please change "–$CH_2C{\equiv}H$" to "–$CH_2C{\equiv}CH$".

This certificate supersedes the Certificate of Correction issued October 16, 2012.

Signed and Sealed this
First Day of January, 2013

David J. Kappos
*Director of the United States Patent and Trademark Office*